US00PP23302P2

(12) United States Plant Patent
Koppe

(10) Patent No.: US PP23,302 P2
(45) Date of Patent: Jan. 1, 2013

(54) ***BEGONIA* PLANT NAMED 'GRACE'**

(50) Latin Name: *Begonia×hiemalis*
Varietal Denomination: Grace

(75) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 30 days.

(21) Appl. No.: 13/134,380

(22) Filed: Jun. 6, 2011

(51) Int. Cl.
*A01H 5/00* (2006.01)

(52) U.S. Cl. ..... Plt./343

(58) Field of Classification Search ..... Plt./343
See application file for complete search history.

*Primary Examiner* — Susan McCormick Ewoldt
(74) *Attorney, Agent, or Firm* — C. A. Whealy

(57) ABSTRACT

A new and distinct cultivar of *Begonia* plant named 'Grace', characterized by its upright, outwardly spreading and mounded plant habit; freely branching habit; dark green-colored leaves; fully double flowers with numerous tepals that are bright red in color and are held above and beyond the foliar plane; and excellent postproduction longevity.

2 Drawing Sheets

Botanical designation: *Begonia×hiemalis.*
Cultivar denomination: 'GRACE'.

BACKGROUND OF THE INVENTION

The present invention relates to a new and distinct cultivar of *Begonia* plant, botanically known as *Begonia×hiemalis*, commercially known as Elatior *Begonia* and hereinafter referred to by the name 'Grace'.

The new *Begonia* plant is a naturally-occurring whole plant mutation of *Begonia×hiemalis* 'Bela Lilacpink', disclosed in U.S. Plant Pat. No. 20,129. The new *Begonia* plant was discovered and selected by the Inventor as a single flowering plant from within a population of plants of 'Bela Lilacpink' in a controlled greenhouse environment in Ermelo, The Netherlands in June, 2008.

Asexual reproduction of the new *Begonia* plant by vegetative cuttings taken in a controlled greenhouse environment in Ermelo, The Netherlands since July, 2008, has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Grace'. These characteristics in combination distinguish 'Grace' as a new and distinct *Begonia* plant:

1. Upright, outwardly spreading and mounded plant habit.
2. Freely branching habit.
3. Dark green-colored leaves.
4. Fully double flowers with numerous tepals that are bright red in color and are held above and beyond the foliar plane.
5. Excellent postproduction longevity.

Plants of the new *Begonia* differ primarily from plants of the parent, 'Bela Lilacpink', in flower color as plants of 'Bela Lilacpink' have dark pink-colored flowers.

Plants of the new *Begonia* can be compared to plants of *Begonia×hiemalis* 'Barkos', disclosed in U.S. Plant Pat. No. 9,523. In side-by-side comparisons conducted in Ermelo, The Netherlands, plants of the new *Begonia* differed primarily from plants of 'Barkos' in leaf serration as leaves of plants of 'Barkos' were not as serrated as leaves of plants of the new *Begonia*. In addition, plants of the new *Begonia* and 'Barkos' differed slightly in flower color.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'Grace' grown in a container.

The photograph on the second sheet are close up views of the upper and lower surfaces of typical leaves (right) and upper, lateral and lower surfaces of developing and open flowers of 'Grace' (left).

DETAILED BOTANICAL DESCRIPTION

The aforementioned photographs and following observations and measurements describe plants grown during the spring in 13-cm containers in a glass-covered greenhouse in Ermelo, The Netherlands and under commercial *Begonia* cultural practices. During the production of the plants, the average day temperature was 20° C. and the average night temperature was 18° C. Plants were twelve weeks old when the photographs and description were taken. In the following description, color references are made to The Royal Horticultural Society Colour Chart, 2007 Edition, except where general terms of ordinary dictionary significance are used.

Botanical classification: *Begonia×hiemalis* 'Grace'.

Commercial classification: Elatior *Begonia*.

Parentage: Naturally-occurring whole plant mutation of *Begonia×hiemalis* 'Bela Lilacpink', disclosed in U.S. Plant Pat. No. 20,129.

Propagation:

*Type*.—By terminal vegetative cuttings.

*Time to develop roots*.—About 20 days at temperatures of 20° C.

*Time to produce a rooted young plant*.—About five weeks at temperatures of 20° C.

*Root description*.—Fine, fibrous; white to orange brown in color.

*Rooting habit*.—Freely branching; medium density; plants of the new *Begonia* have not been observed to form tubers.

Plant description:

*Plant form*.—Upright, outwardly spreading and mounded plant habit, inverted triangle; freely branching with good stem and stem base strength; flowers are double and positioned above the foliar plane.

*Growth habit*.—Moderately vigorous growth habit; suitable for 13-cm and larger containers; under optimal environmental and cultural conditions, usually about twelve weeks are required to produce proportional 13-cm potted plants from cuttings; vegetative shoots are formed at basal nodes and flowering shoots are formed at upper nodes.

*Plant height*.—About 26.1 cm.

*Plant width*.—About 34 cm.

*Lateral branches*.—Length: About 10.6 cm. Diameter: About 9 mm. Internode length: About 1.9 cm. Angle: About 40° from vertical. Texture: Smooth, glabrous. Color: Close to 146B to 146C heavily tinged with close to 176C.

*Leaves*.—Arrangement: Alternate; simple. Length: About 10.8 cm. Width: About 11.3 cm. Shape: Deltoid to reniform. Apex: Acute. Base: Cordate; asymmetric. Margin: Bi-serrate. Texture, upper surface: Smooth, glabrous; velvety. Texture, lower surface: Sparsely pubescent. Venation pattern: Palmate. Color: Developing leaves, upper surface: Close to N137C to N137D. Developing leaves, lower surface: Close to 148B. Fully expanded leaves, upper surface: Darker than between 139A and 147A; venation, close to 143A. Fully expanded leaves, lower surface: Close to 148B; venation, close to 144A. Petioles: Length: About 4.7 cm. Diameter: About 6 mm by 5 mm. Texture, upper and lower surfaces: Smooth, glabrous. Color, upper surface: Close to 176A. Color, lower surface: Close to 176B to 176C. Stipules: Length: About 1 cm. Width: About 5 mm. Shape: Ovate. Apex: Acute. Base: Broadly cuneate. Margin: Entire. Texture, upper and lower surfaces: Smooth, glabrous. Color, upper and lower surfaces: Close to 143C.

Flower description:

*Flowering habit*.—Double flowers with tepals arranged in axillary compound cymes; usually eight flowers per cyme; about 160 flowers develop per plant; numerous cymes in flower simultaneously; flowers face upright to outwardly and are positioned above and beyond the foliar plane.

*Natural flowering season*.—Plants begin flowering about six weeks after pinching; plants flower continuously year round regardless of nyctoperiod, however plants flower earlier and more abundantly from mid-February until November in the Northern Hemisphere.

*Flower longevity*.—Individual flowers last about ten days on the plant; flowers not persistent; flowering plants have excellent postproduction longevity and typical maintain good substance for about six weeks under interior conditions.

*Inflorescence height*.—About 13.6 cm.

*Inflorescence diameter*.—About 13.4 cm.

*Flower buds*.—Length: About 1.6 cm. Diameter: About 1.1 cm to 1.4 cm. Shape: Broadly obovate, flattened. Color: Between 146D and 152D heavily tinged with between 53A and 185A.

*Flowers*.—Shape: Rounded; fully double; rose-like. Diameter: About 6.8 cm. Depth (height): About 3.8 cm.

*Tepals and tepaloids*.—Arrangement: Rosette. Quantity per flower: Numerous, typically about 48 per flower in multiple whorls. Length: About 3.2 cm to 3.8 cm. Width: About 2.9 cm to 4 cm. Shape: Broadly obcordate to obcordate. Apex: Rounded. Margin: Laciniate. Texture, upper and lower surfaces: Smooth, glabrous; velvety. Color: When opening, upper surface: Close to 53A; towards the base, close to 53B to 53C. When opening, lower surface: Close to 53B; towards the base, close to 53D. Fully opened, upper surface: Close to 46B; towards the base, close to 53C. Fully opened, lower surface: Close to 47A; towards the base, between 47B and 53D; outer petals with random sectors of close to 148B.

*Flower bracts*.—Quantity and arrangement: Two, opposite; sessile. Length: About 2.9 cm. Width: About 2.3 cm. Shape: Obovate. Apex: Acute. Margin: Entire. Texture, upper and lower surfaces: Smooth, glabrous; velvety. Color, upper surface: Close to 53A to 53D marbled with close to 143A. Color, lower surface: Close to 146B; towards the margins, close to 53A.

*Peduncles*.—Length: About 8.3 cm. Angle: About 40° from vertical. Texture: Smooth, glabrous. Color: Close to 152A to 152B.

*Pedicels*.—Length: About 3.5 cm. Angle: Erect. Texture: Smooth, glabrous. Color: Between 174B and 177B.

*Reproductive organs*.—Stamens: None observed. Pistils: If present, deformed. Stigma: Not observed. Style length: About 3 mm. Style color: Close to 179D. Ovary: Not observed.

*Seeds and fruits*.—Seed and fruit production have not been observed.

Disease/pest resistance: Resistance to pathogens and pests common to *Begonia* has not been observed.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'Grace' as illustrated and described.

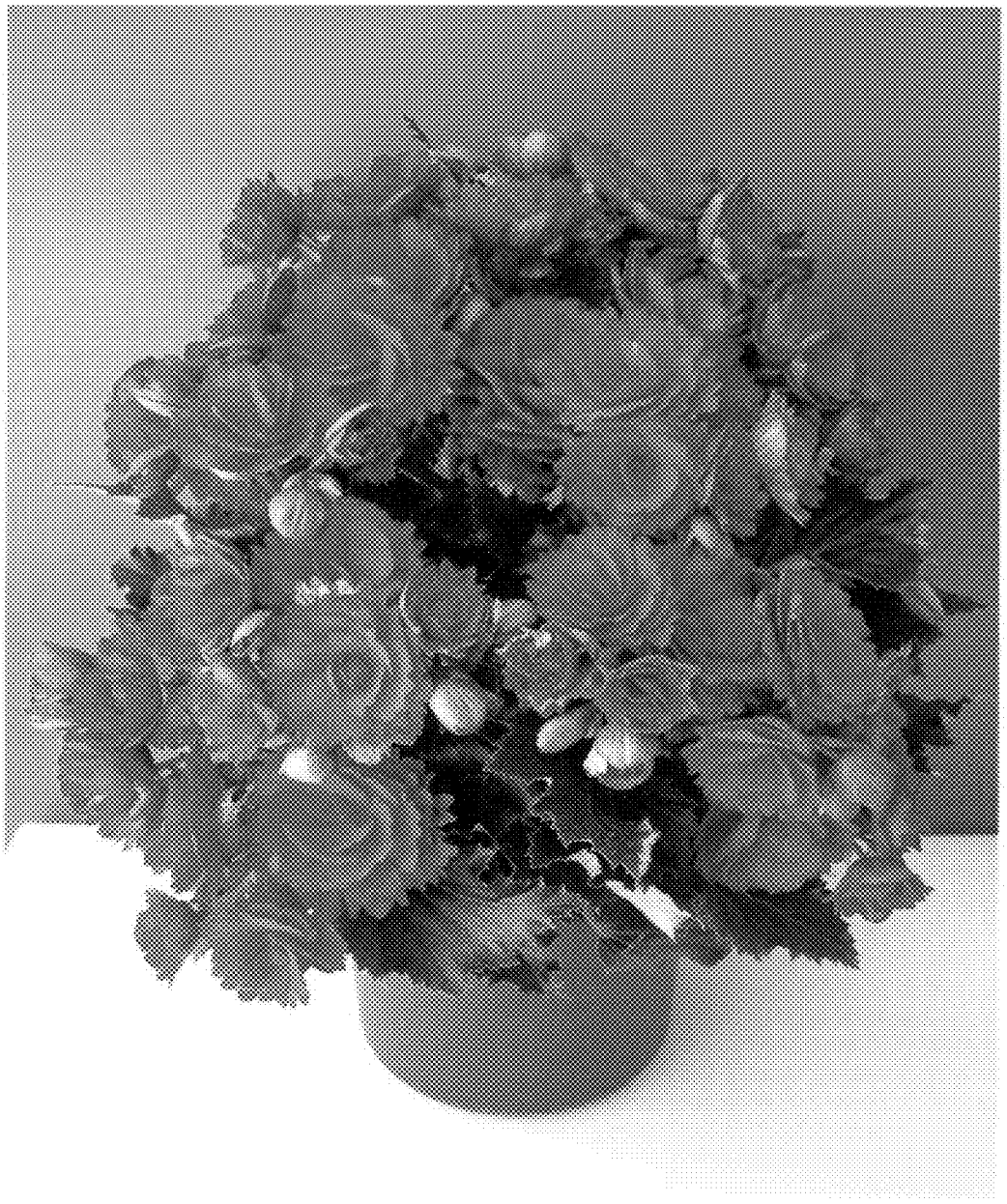

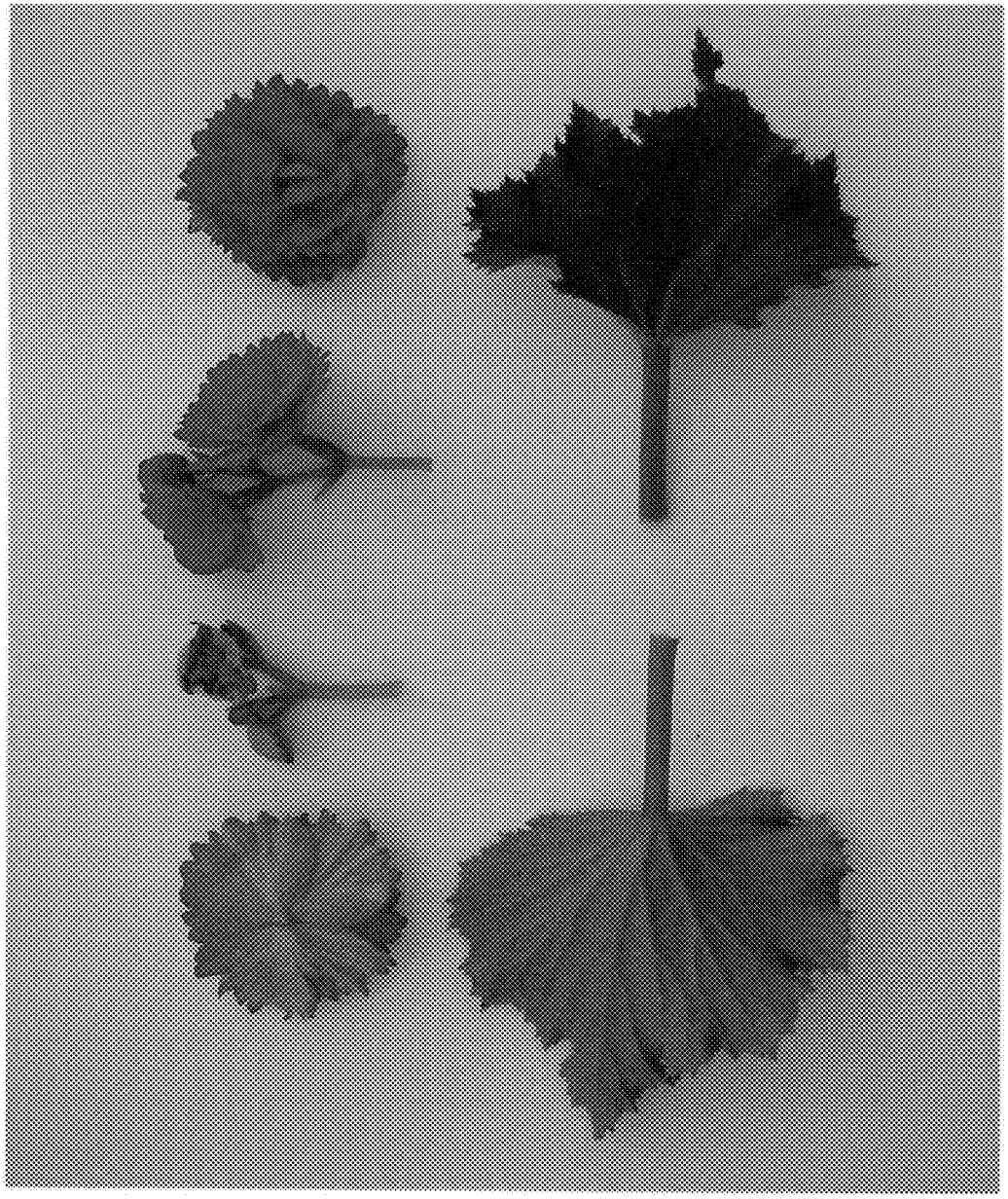

* * * * *